United States Patent [19]

Sprecker et al.

[11] Patent Number: 4,524,020
[45] Date of Patent: Jun. 18, 1985

[54] ISOPROPYL SUBSTITUTED CYCLOHEXENYL METHYL KETONES AND PERFUMERY USES THEREOF

[75] Inventors: Mark A. Sprecker, Sea Bright; Robert P. Belko, Woodbridge, both of N.J.; Augustinus G. Van Loveren, Ryebrook, N.Y.; Marie R. Hanna, Hazlet, N.J.

[73] Assignee: International Flavors & Fragrances Inc., New York, N.Y.

[21] Appl. No.: 643,827

[22] Filed: Aug. 24, 1984

[51] Int. Cl.³ .......................... A61K 7/46; C07C 49/21
[52] U.S. Cl. ................................. 252/522 R; 252/89.1; 252/108; 514/690; 568/377
[58] Field of Search ................... 568/376, 377, 378; 252/522, 891, 108; 424/70

[56] References Cited

U.S. PATENT DOCUMENTS

| 3,953,516 | 4/1976 | Corbier et al. | 568/377 |
| 3,975,310 | 8/1976 | Kovats et al. | 568/374 |
| 4,018,479 | 3/1978 | Hall et al. | 568/376 |
| 4,119,577 | 10/1978 | Light et al. | 568/820 |
| 4,187,251 | 2/1980 | Sleppnik | 568/376 |
| 4,289,659 | 9/1981 | Schulte-Elte et al. | 568/376 |
| 4,424,379 | 1/1984 | Sprecker et al. | 568/376 |

OTHER PUBLICATIONS

Pishnamazzada et al., Vop. Neflekhim, 1971, pp. 158–162, (1971).
Kugatova et al., Chem. Abst., vol. 74, #111623c, (1971).
Arctander, "Perfume and Flavor Chemicals", Monograph 1000, (1969).

Primary Examiner—James H. Reamer
Attorney, Agent, or Firm—Arthur L. Liberman

[57] ABSTRACT

Described are isopropyl substituted cyclohexenyl methyl ketones defined according to the structure:

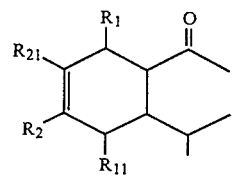

wherein $R_1$, $R_2$, $R_{11}$ and $R_{21}$ each represents hydrogen or methyl with the provisos that:
(a) at least two of $R_1$, $R_{21}$, $R_2$ and $R_{11}$ represent hydrogen;
(b) either $R_2$ is methyl and $R_{21}$ is hydrogen or $R_{21}$ is methyl and $R_2$ is hydrogen; and
(c) $R_1$ is methyl only when $R_2$ is methyl and $R_{11}$ is methyl only when $R_{21}$ is methyl, as well as uses thereof in augmenting or enhancing the aroma of perfume compositions, colognes and perfumed articles including solid or liquid anionic, cationic, nonionic or zwitterionic detergents, fabric softener compositions, fabric softener articles, hair preparations and perfumed polymers.

11 Claims, 12 Drawing Figures

GLC PROFILE FOR EXAMPLE II. CRUDE

GLC PROFILE FOR EXAMPLE I. CRUDE

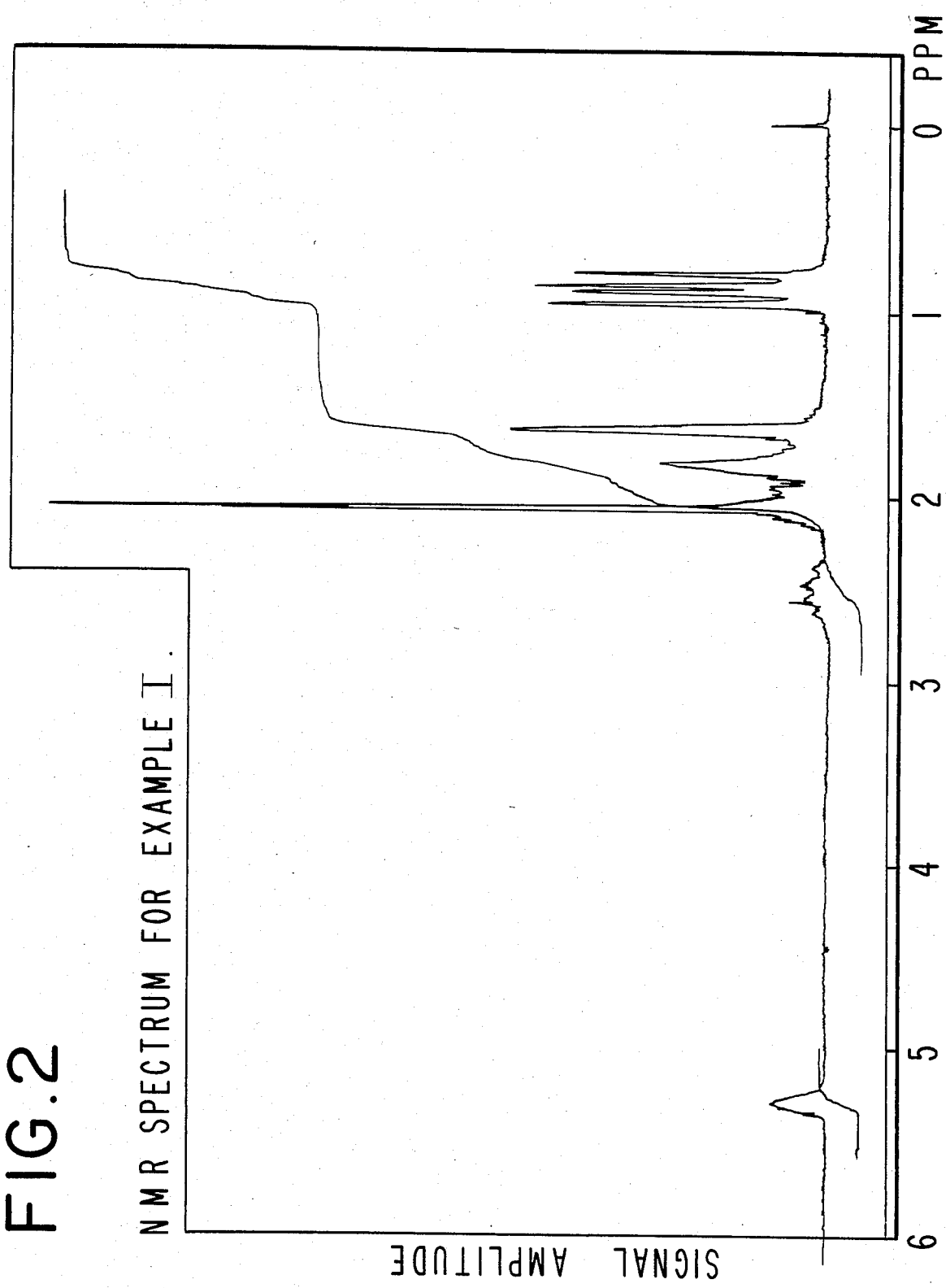
FIG. 2 NMR SPECTRUM FOR EXAMPLE I.

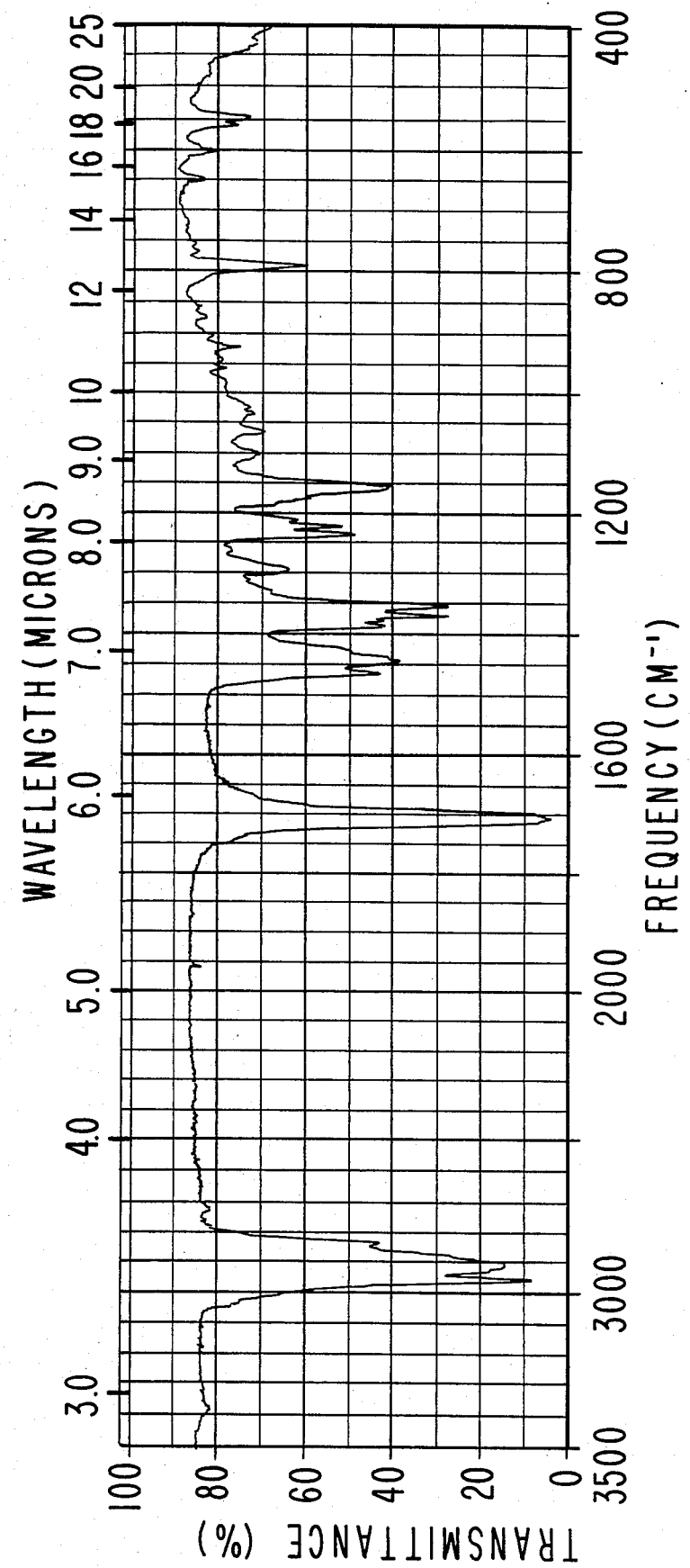

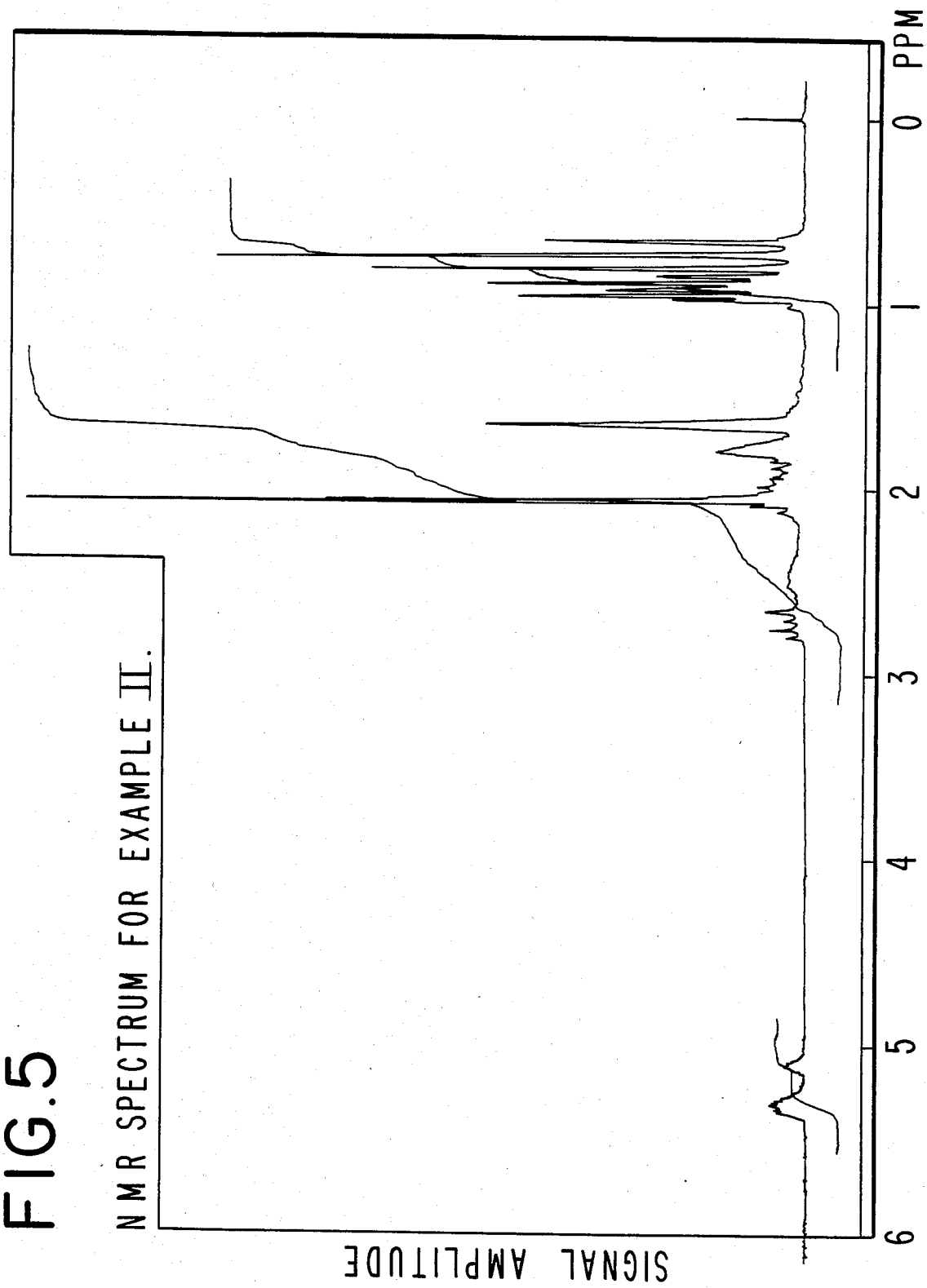

IR SPECTRUM FOR EXAMPLE II.

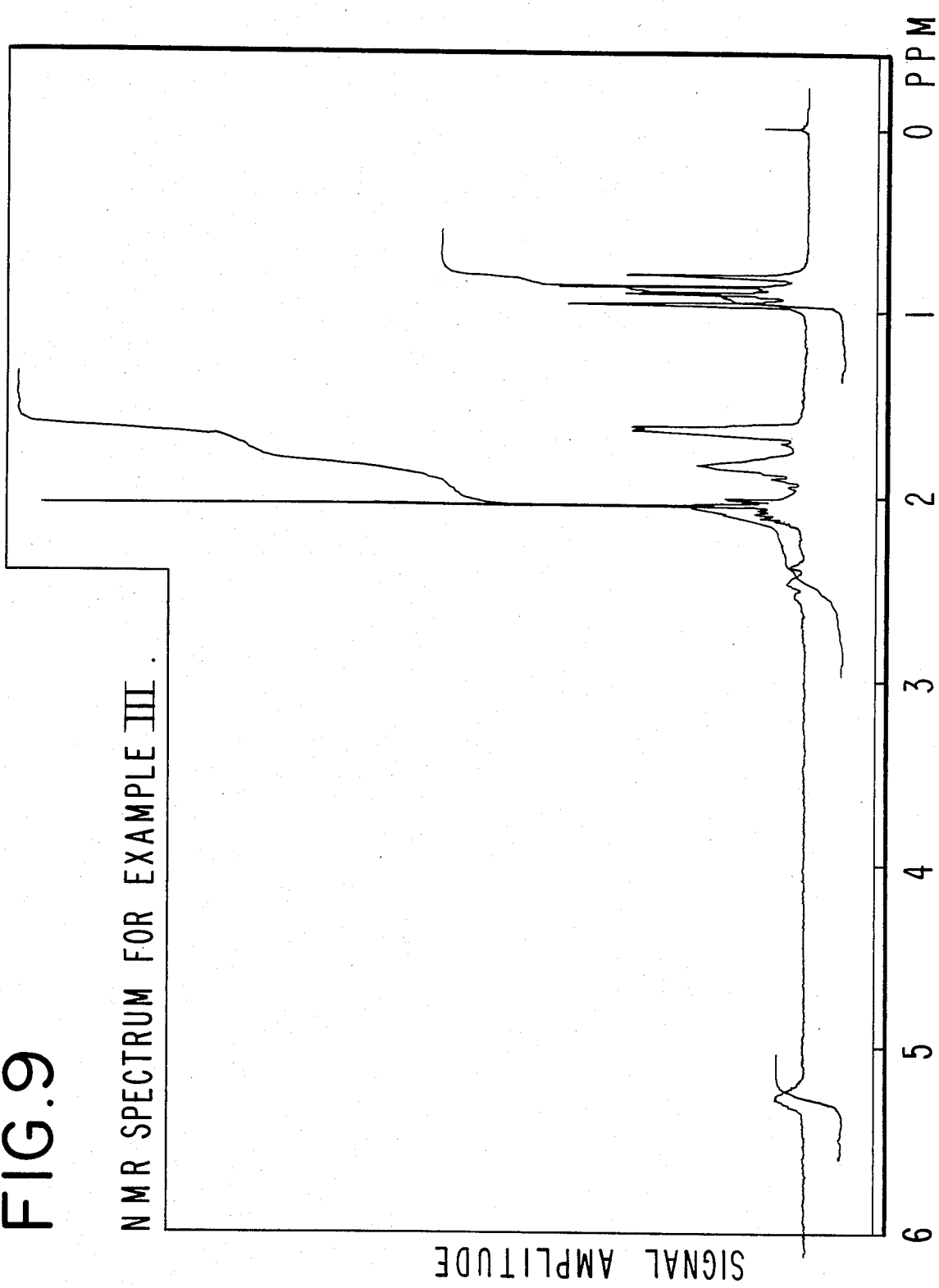

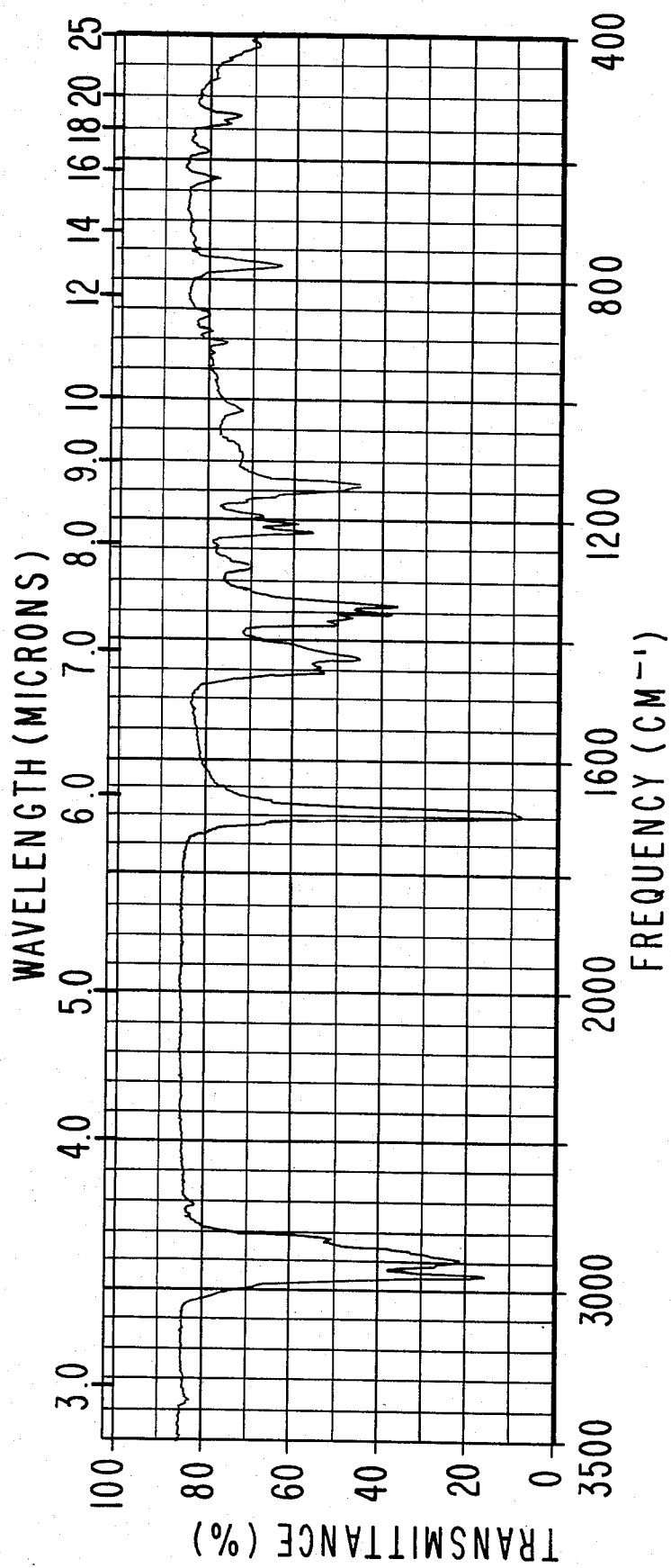

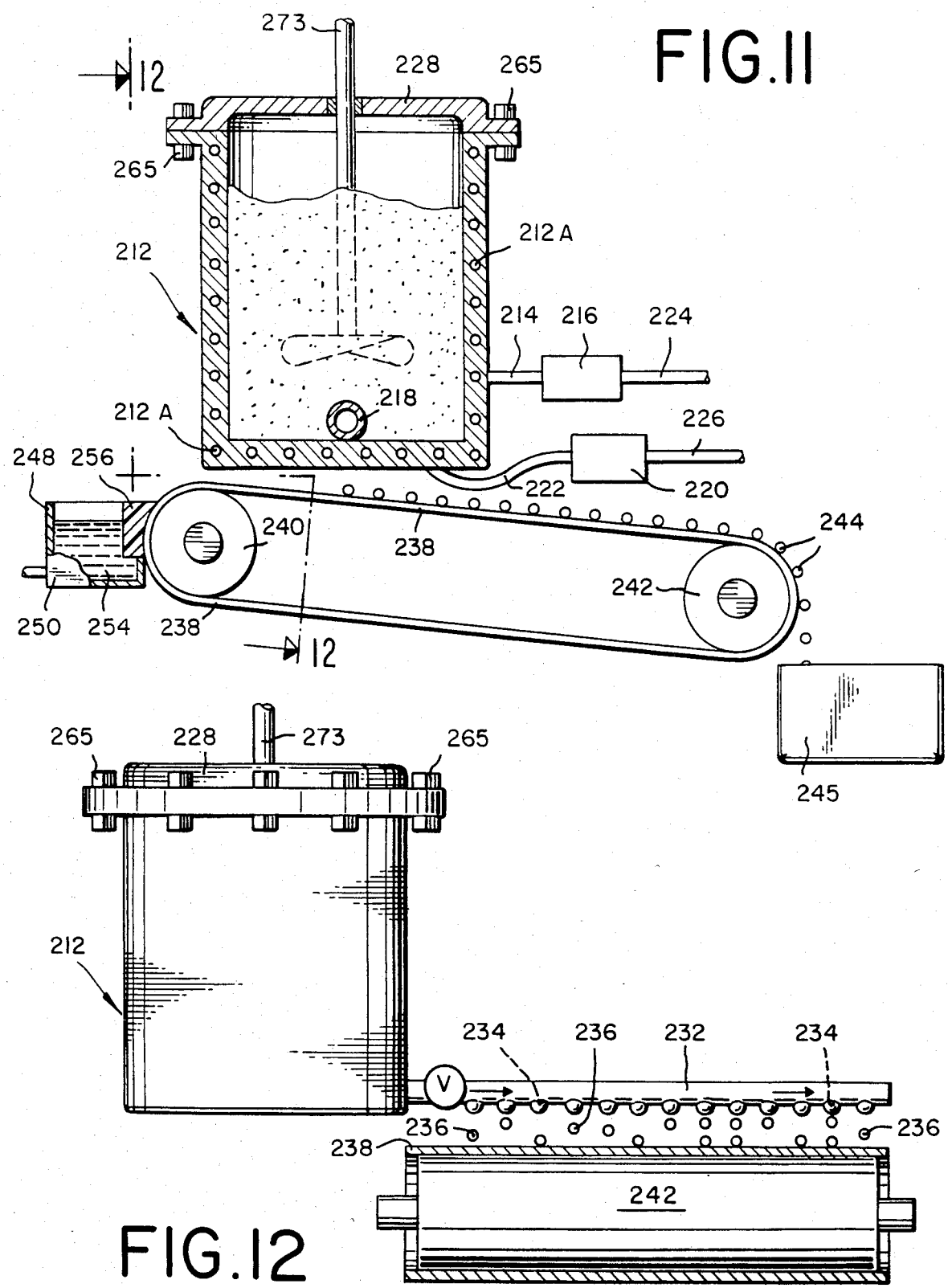

ISOPROPYL SUBSTITUTED CYCLOHEXENYL METHYL KETONES AND PERFUMERY USES THEREOF

BACKGROUND OF THE INVENTION

The instant invention provides the isopropyl substituted cyclohexenyl methyl ketones defined according to the structure:

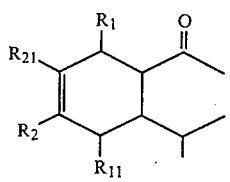

wherein $R_1$, $R_2$, $R_{11}$ and $R_{21}$ each represents hydrogen or methyl with the provisos that:

(a) at least two of $R_1$, $R_{21}$, $R_2$ and $R_{11}$ represent hydrogen;
(b) either $R_2$ is methyl and $R_{21}$ is hydrogen or $R_{21}$ is methyl and $R_2$ is hydrogen; and
(c) $R_1$ is methyl only when $R_2$ is methyl and $R_{11}$ is methyl only when $R_{21}$ is methyl and uses thereof for their organoleptic properties in consumable materials.

Substances which provide powerful musty, musky, camphoraceous, rosy, green, spicy (cubeb/peppery), woody and caryophyllene-like aromas with buttery and spicy topnotes are highly desirable in the art of perfumery. Many of the natural materials which provide such fragrances and contribute such desired nuances to perfumery compositions are high in cost, vary in quality from one batch to another and/or are generally subject to the usual variations of natural products.

Methyl substituted acetyl cyclohexene derivatives are well known in the art of perfumery.

Thus, Arctander "Perfume and Flavor Chemicals (Aroma Chemicals)", Volume I, at Monograph 1000 describes the perfumery utilities of 1,1-dimethyl-cycolhex-3-enyl methyl ketone defined according to the structure:

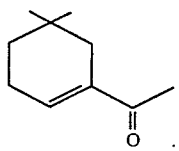

At Monograph 1000, Arctander states that the compound having the structure:

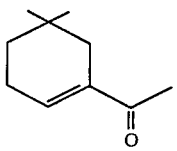

has a powerful, herbaceous, somewhat weedy, but basically sweet odor of moderate tenacity. Arctander states that this ketone occurs as a minor component in the reaction mixture from treatment of myrcene hydrochloride with acetylating agents.

Methyl substituted acetyl cyclohexene derivatives are also known as intermediates for preparation of other perfumery materials. Thus, the compounds having the structures:

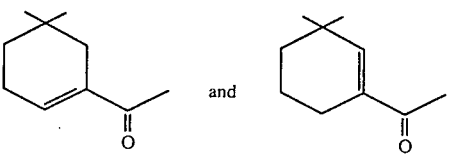

are described in U.S. Pat. No. 4,289,659 issued on Sept. 15, 1981 (Schulte-Elte, et al).

Furthermore, the genus of compounds defined according to the structure:

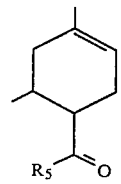

wherein $R_5$ represents methylethyl or propyl are disclosed as intermediates for the preparation of synthetic plant growth promoters by Kujatova-Shemyakina, et al, Chem.Abstracts, Volume 74, 1971, 111613c.

The compounds of our invention are produced via a Diels-Alder reaction between a diene such as isoprene or methyl isoprene and a dienophile which is a ketone, specifically 2-methyl-3-hexen-5-one according to the reaction:

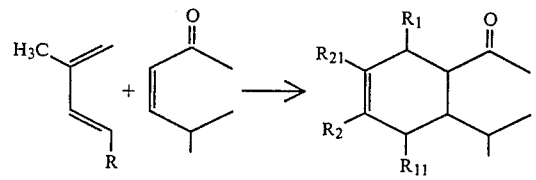

wherein R represents methyl or ethyl and $R_1$, $R_{21}$, $R_2$ and $R_{11}$ have been defined, supra. The reaction of our invention can be carried out thermally at higher temperatures or in the presence of a Lewis acid catalyst at lower temperatures. The prior art contains reactions between aldehyde dienophiles and isoprene derivatives, for example, the reaction:

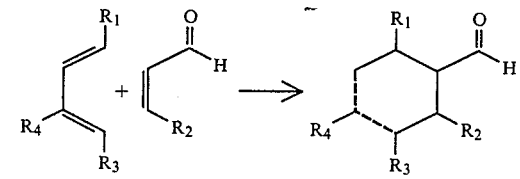

as disclosed in U.S. Pat. No. 4,424,379, at columns 14 and 15 thereof.

The resulting aldehydes in U.S. Pat. No. 4,424,379 are used for their properties as intermediates in producing perfumery materials by means of such reactions as aldol condensations.

Nothing in the prior art however, implicitly or explicitly indicates that the isopropyl substituted cyclohexenyl methyl ketones of our invention or compounds obvious to the isopropyl substituted cyclohexenyl methyl ketones of our invention are useful for their organoleptic properties particularly in augmenting or enhancing the aroma of perfume compositions, colognes and/or perfumed articles.

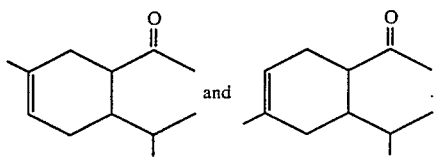

FIG. 2 is the NMR spectrum for the mixture of "cis" and "trans" isomers of the compounds having the structures:

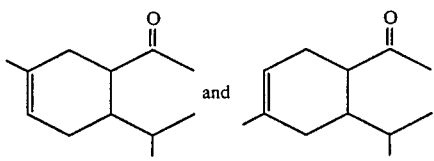

produced according to Example I (conditions: Field strength: 100 MHz; Solvent: CFCl$_3$).

FIG. 3 is the infra-red spectrum for the mixture of "cis" and "trans" isomers having the structures:

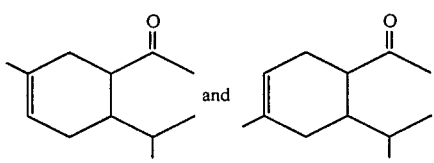

produced according to Example I.

Figure 4:
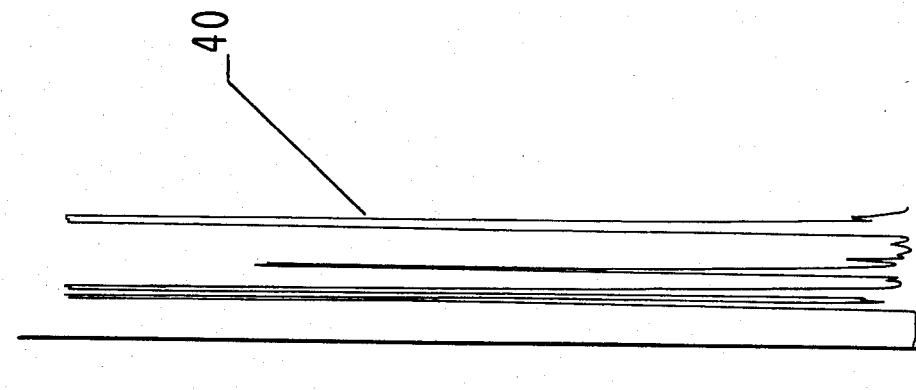

FIG. 4 is the GLC profile for the crude reaction product produced according to Example II which contains a mixture of "cis" and "trans" isomers of the compounds having the structures:

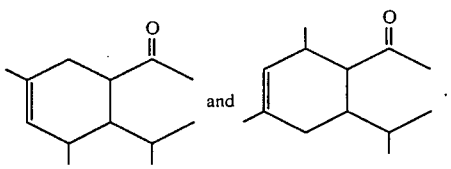

FIG. 5 is the NMR spectrum for the mixture of "cis" and "trans" isomers of the mixture of compounds having the structures:

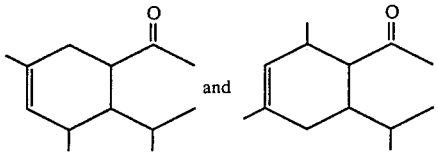

produced according to Example II.

Figure 6:
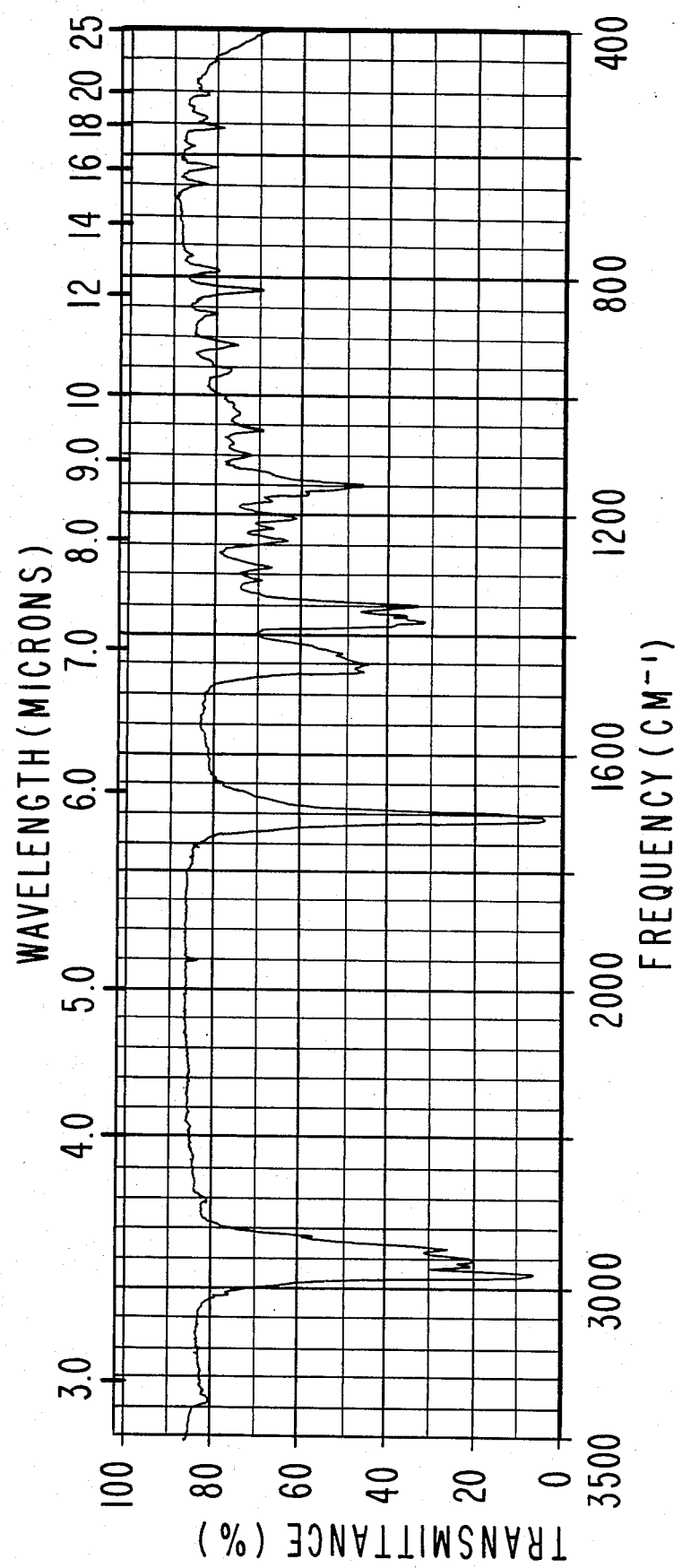

FIG. 6 is the infra-red spectrum for the mixture of "cis" and "trans" isomers of the mixture of compounds having the structures:

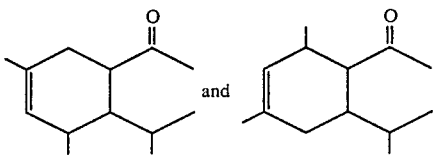

produced according to Example II.

Figure 7:
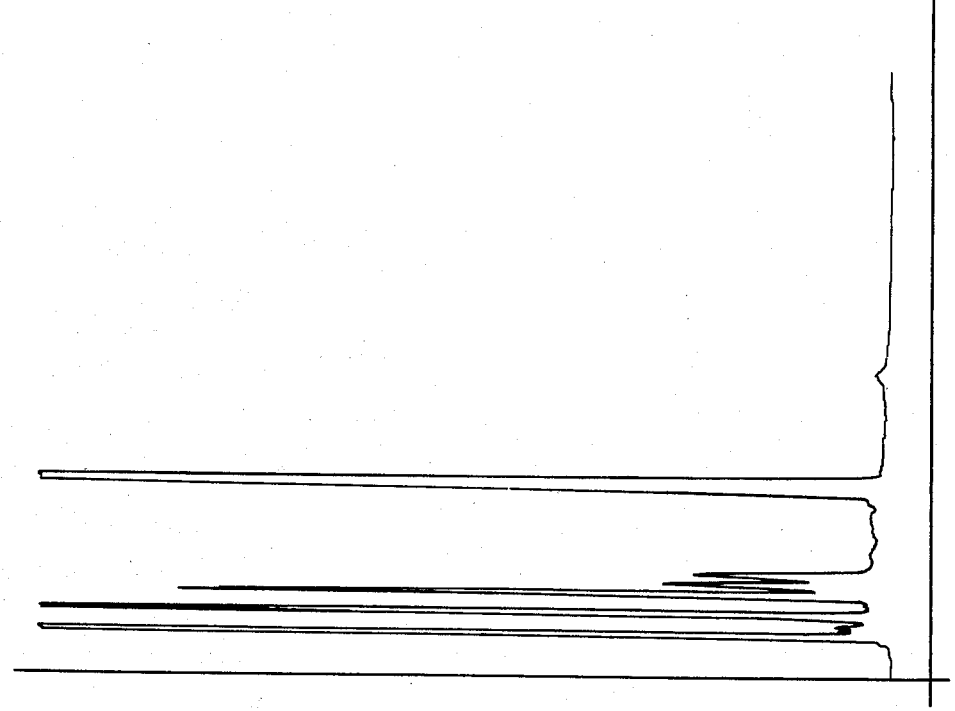

FIG. 7 is the GLC profile for the crude reaction product produced according to Example III which is a mixture of "cis" and "trans" isomers of the compound having the structure:

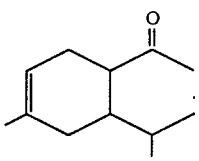

Figure 8:
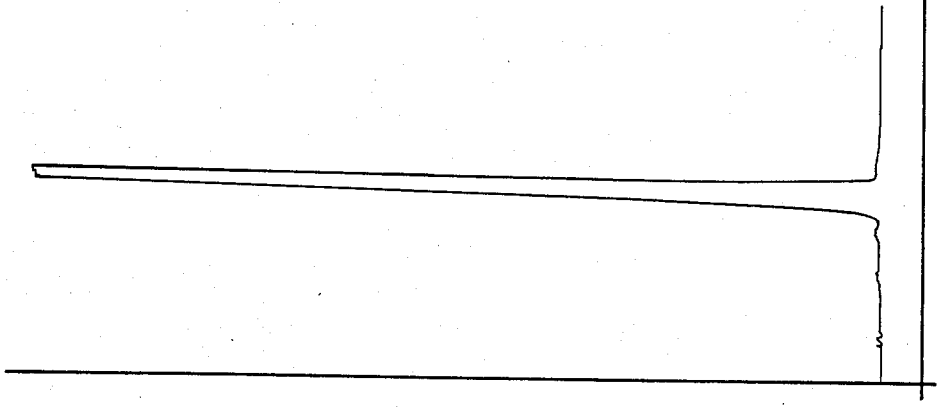

FIG. 8 is the GLC profile for bulked distillation fractions 10-19 of the distillation of the reaction product of Example III which contains the "cis" and "trans" isomers of the compound having the structure:

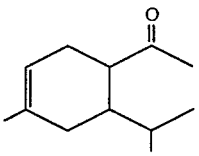

prepared according to Example III.

FIG. 9 is the NMR spectrum for the "cis" and "trans" isomers of the compound having the structure:

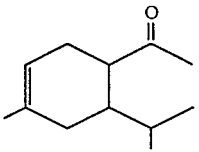

prepared according to Example III (conditions: Field strength: 100 MHz; Solvent: CFCl$_3$).

FIG. 10 is the infra-red spectrum for the "cis" and "trans" isomers of the compound having the structure:

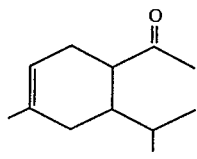

produced according to Example III.

FIG. 11 is a cut-away side elevation view of the apparatus employed in forming a perfumed polymer of our invention which perfumed polymer contains at least tone of the isopropyl substituted cyclohexenyl methyl ketones defined according to the structure:

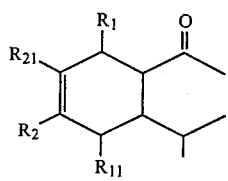

wherein $R_1$, $R_2$, $R_{11}$ and $R_{21}$ each represents hydrogen or methyl with the provisos that:
  (a) at least two of $R_1$, $R_{21}$, $R_2$ and $R_{11}$ represent hydrogen;
  (b) either $R_2$ is methyl and $R_{21}$ is hydrogen or $R_{21}$ is methyl and $R_2$ is hydrogen; and
  (c) $R_1$ is methyl only when $R_2$ is methyl and $R_{11}$ is methyl only when $R_{21}$ is methyl.

FIG. 12 is a side elevation view of the apparatus of FIG. 11 taken along lines 12—12 of FIG. 11.

DETAILED DESCRIPTION OF THE DRAWINGS

Figure 1:
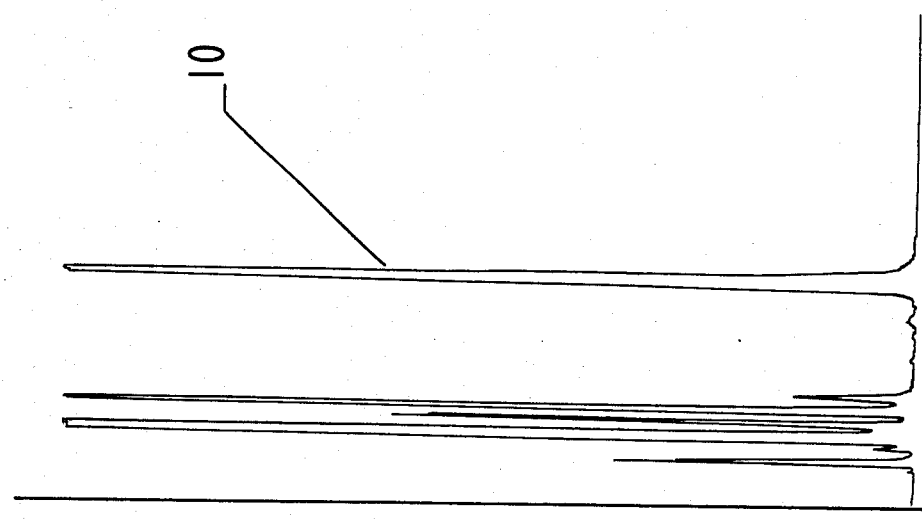
FIG. 1 is the GLC profile for the crude reaction product produced according to Example I containing the "cis" and "trans" isomers of the compounds having the structures.

FIG. 1 is the GLC profile for the crude reaction product of Example I containing the compounds having the structures:

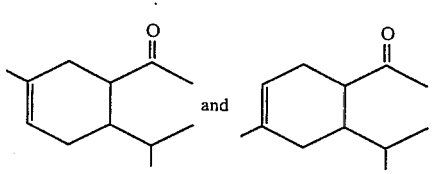

(mixtures of "cis" and "trans" isomers of each). The peak indicated by the reference numeral "10" is the peak for the product having the structures:

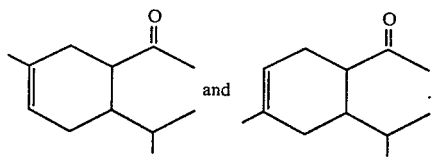

The "cis" isomer of the compound having the structure:

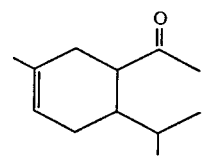

has the structure:

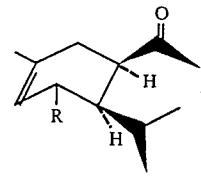

The "trans" isomer of the compound having the structure:

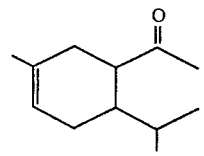

has the structure:

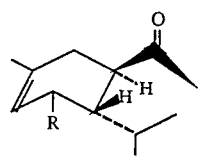

wherein R in each of the cases represents hydrogen. On the other hand, the "cis" isomer of the compound having the structure:

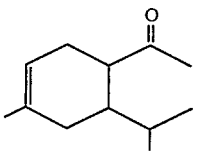

has the structure:

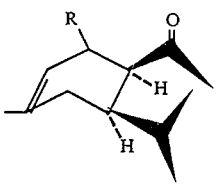

and the "trans" isomer of the compound having the structure:

has the structure:

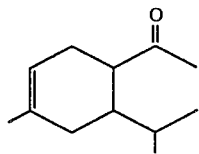

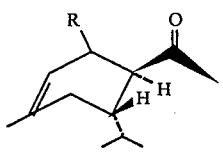

wherein R in each of the cases represents hydrogen. (Conditions: SE-30 column programmed at 180° C. isothermal.)

FIG. 4 is the GLC profile for the crude reaction product of Example II containing the "cis" and "trans" isomers of the compounds having the structures:

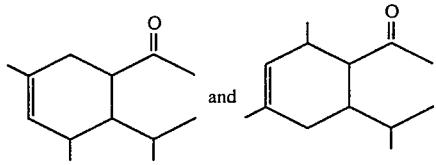

The peak indicated by reference numeral "40" is the peak for the product of the reaction which is the mixture of "cis" and "trans" isomers of the compounds having the structures:

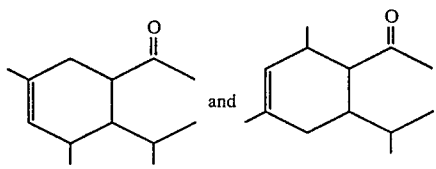

The "cis" isomer of the compound having the structure:

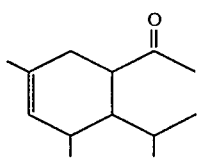

is represented by the structure:

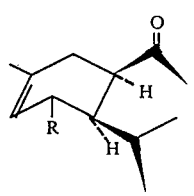

wherein R is methyl. The "trans" isomer of the compound having the structure:

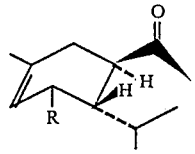

is represented by the structure:

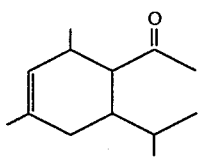

wherein R represents methyl. The "trans" isomer of the compound having the structure:

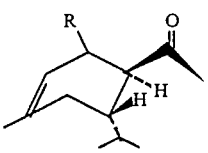

is represented by the structure:

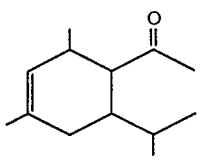

wherein R is methyl. The "cis" isomer of the compound having the structure:

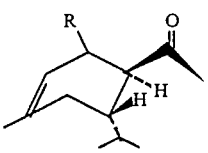

is represented by the structure:

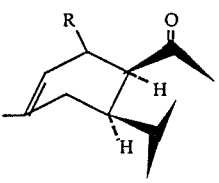

wherein R is methyl. (Conditions: SE-30 column programmed at 150° C. isothermal.)

Referring to FIGS. 11 and 12, which show the apparatus for preparing scented polymers such as polyethylene, a quantity of thermoplastic polymer having a melting point of 220°–250° F. is placed in container 212 as illustrated in FIGS. 11 and 12. 25 Pounds of a perfume formulation containing at least one of the isopropyl substituted cyclohexenyl methyl ketones of our invention is then quickly added to the liquified molten polymer in container 212, the lid 228 is put in place and the agitating means 273 is actuated. The temperature is maintained at about 225° C. and the mixing is continued for about 10 minutes. The valve "V" is then opened to allow flow of the molten termoplastic polymer (e.g., polyethylene or polypropylene) enriched with a scent-imparting substance containing at least one of the isopropyl substituted cyclohexenyl methyl ketones of our invention, to exit through orifices 234. The liquid falling through orifices 234 solidifies almost instantaneously upon impact of the moving cooled conveyor 238. Thermoplastic polymer (e.g., polyethylene) beads or pellets 224 having a pronounced scent as described in the examples, infra, resulting from the composition containing one of the isopropyl substituted cyclohexenyl methyl ketones of our invention are thus formed. Analysis demonstrates that the pellets contain about 25% of a scent-imparting material containing one of the isopropyl substituted cyclohexenyl methyl ketones of our invention so that almost no loss in the scenting substance occurs. The pellets are used as set forth, infra. The conveyor belt 238 is driven by rollers 240 and 242 with cooling apparatus 250 next to roller 240. The tank 212 is heated with heating elements 212A which are energized using an electrical energy source connected via wires 214 and 222 through wires 224 and 226. The solidified pellets are collected in container 245 for subsequent utilization as set forth in the examples, infra.

THE INVENTION

This invention relates to the novel isopropyl substituted cyclohexenyl methyl ketones defined according to the structure:

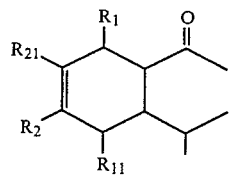

wherein $R_1$, $R_2$, $R_{11}$ and $R_{21}$ each represents hydrogen or methyl with the provisos that:
(a) at least two of $R_1$, $R_{21}$, $R_2$ and $R_{11}$ represent hydrogen;
(b) either $R_2$ is methyl and $R_{21}$ is hydrogen or $R_{21}$ is methyl and $R_2$ is hydrogen; and
(c) $R_1$ is methyl only when $R_2$ is methyl and $R_{11}$ is methyl only when $R_{21}$ is methyl,
and uses thereof in augmenting or enhancing a variety of fragrances of various consumable materials.

Briefly, our invention contemplates augmenting or enhancing fragrances of such consumable materials as perfume compositions, perfumed articles (e.g., solid or liquid anionic, cationic, nonionic or zwitterionic detergents, fabric softeners, fabric softener articles, cosmetic powders, hair preparations such as shampoos and perfumed thermoplastics and thermosetting resins), and colognes by adding thereto a small but effective amount of at least one of the isopropyl substituted cyclohexenyl methyl ketones of our invention having the structure:

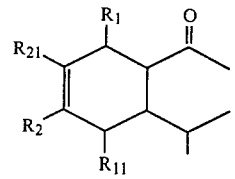

wherein $R_1$, $R_2$, $R_{11}$ and $R_{21}$ each represents hydrogen or methyl with the provisos that:
(a) at least two of $R_1$, $R_{21}$, $R_2$ and $R_{11}$ represent hydrogen;
(b) either $R_2$ is methyl and $R_{21}$ is hydrogen or $R_{21}$ is methyl and $R_2$ is hydrogen; and
(c) $R_1$ is methyl only when $R_2$ is methyl and $R_{11}$ is methyl only when $R_{21}$ is methyl.

The isopropyl substituted cyclohexenyl methyl ketones of our invention augment or enhance musty, musky, camphoraceous, rosy, green, spicy (cubeb/peppery), woody and caryophyllene-like aromas with buttery and spicy topnotes. The isopropyl substituted cyclohexenyl methyl ketones of our invention augment, enhance or impart such aroma nuances in or to perfumes, perfumed articles and colognes.

The isopropyl substituted cyclohexenyl methyl ketones of our invention are produced by means of a Diels-Alder reaction of an isoprene derivative having the structure:

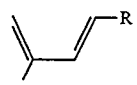

wherein R represents hydrogen or methyl with 2-methyl-3-hexen-5-one according to the reaction:

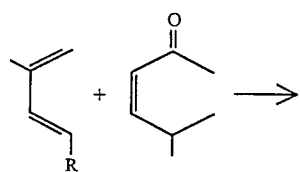

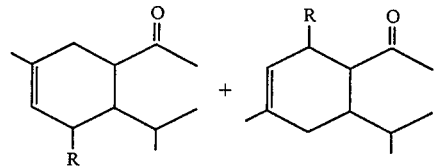

when the reaction is a "thermal" Diels-Alder reaction and according to the reaction:

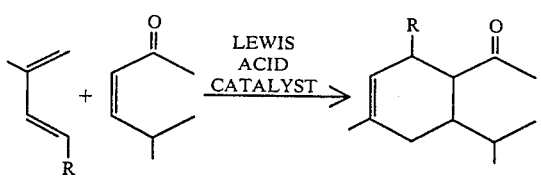

when the reaction is a low temperature catalyzed Diels-Alder reaction.

When carrying out the "catalyzed Diels-Alder reaction; that is, catalyzed using a Lewis acid catalyst, the compound formed has the structure:

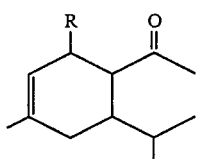

and substantially no compound having the structure:

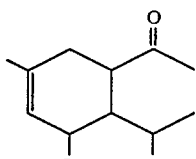

is present in the reaction mass. On the other hand, when using a thermal Diels-Alder reaction at higher temperatures mixtures of the compounds having the structures:

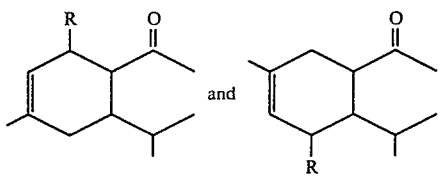

are formed. In all cases, however, "cis" and "trans" isomers are formed having the structures:

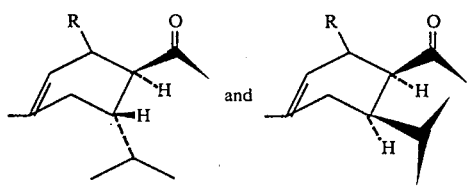

wherein R represents hydrogen or methyl. In the case of the thermal Diels-Alder reaction, compounds having the structures:

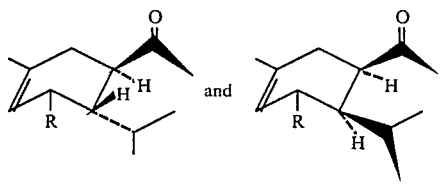

are also formed.

As will be seen in the examples, infra, the reaction product of the Diels-Alder reaction carried on at lower temperatures using a catalyst have aroma nuances different from the reaction products of the Diels-Alder reaction carried out "thermally" at higher temperatures in the absence of a catalyst.

When the Diels-Alder reaction is carried at lower temperatures, a Lewis acid catalyst is used such as stannic chloride, zinc chloride, aluminum diethyl chloride or ethyl aluminum dichloride (e.g., at temperatures of 10°–40° C.).

When carrying out the thermal Diels-Alder reaction, according to the reaction:

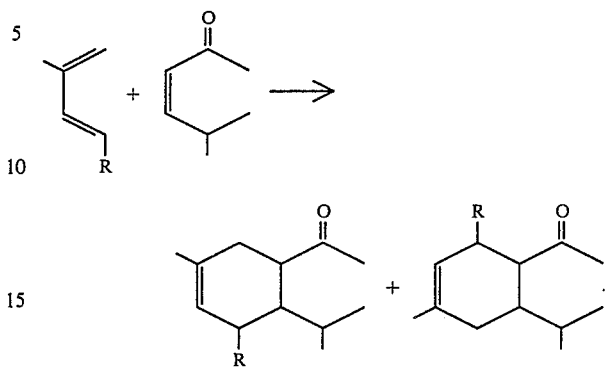

The reaction is carried out at higher temperatures, e.g., 140°–200° C. and pressures higher than atmospheric, e.g., about 100 psig up to about 400 psig.

At the end of each of the Diels-Alder reactions, whether catalytic or high pressure, high temperature (thermal), the reaction mass is "worked up" by means of fractional distillation. The resulting fractions are then utilized in perfume compositions, colognes and/or perfumed articles for their specific aroma nuances.

Examples of the isopropyl substituted cyclohexenyl methyl ketones of our invention and their perfumery properties are as follows:

TABLE I

| Structure of Compounds | Fragrance Characteristics |
|---|---|
| A mixture of compounds having the structures: <br><br> ("cis" and "trans" isomers of each) prepared according to Example I. | A musty, musky, camphoraceous, rosy and green aroma profile. |
| A mixture of compounds having the structures: <br><br> ("cis" and "trans" isomers) prepared according to Example II. | A spicy (cubeb/peppery), woody, camphoraceous and caryophyllene-like aroma profile. |

TABLE I-continued

| Structure of Compounds | Fragrance Characteristics |
|---|---|
| A mixture of compounds defined according to the structure: 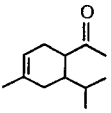 ("cis" and "trans" isomers) prepared according to Example III via a catalytic Diels-Alder reaction. | A green, woody, rosy, musty and camphoraceous aroma with buttery and spicy topnotes. |

Stated, supra, the isopropyl substituted cyclohexenyl methyl ketones of our invention can be used to augment, enhance or impart musty, musky, camphoraceous, rosy, green, spicy (cubeb/peppery), woody and caryophyllene-like aroma nuances with buttery and spicy topnotes to perfume compositions, perfumed articles and colognes.

As olfactory agents the isopropyl substituted cyclohexenyl methyl ketones of our invention can be formulated into or used as components of a "perfume composition" or can be used as components of a "perfumed article" or the perfume composition may be added to "perfumed articles".

The term "perfume composition" is used herein to mean a mixture of organic compounds including, for example, alcohols, aldehydes, ketones other than the ketones of our invention, nitriles, ethers, lactones, natural essential oils, synthetic essential oils and frequently hydrocarbons which are admixed so that the combined odors of the individual components produce a pleasant or desired fragrance. Such perfume compositions usually contain: (a) the main note or the "bouquet" or foundation-stone of the composition; (b) modifiers which round-off and accompany the main note; (c) fixatives which include odorous substances which lend a particular note to the perfume throughout all stages of evaporation, and substances which retard evaporation; and (d) topnotes which are usually low-boiling, fresh-smelling materials.

In perfume compositions, the individual component will contribute its particular olfactory characteristics, but the overall effect of the perfume composition will be the sum of the effects of each of the ingredients. Thus, the individual isopropyl substituted cyclohexenyl methyl ketones of our invention, or mixtures thereof, can be used to alter the aroma charatistics of a perfume composition, for example, by highlighting or moderating the olfactory reaction contributed by another ingredient in the composition.

The amount of one or more of the isopropyl substituted cyclohexenyl methyl ketones of our invention which will be effective in perfume compositions depends on many factors, including the other ingredients, their amounts and the effects which are desired. It has been found that perfume compositions containing as little as 0.05% of the isopropyl substituted cyclohexenyl methyl ketones of our invention, or even less, can be used to impart, augment or enhance, interesting, musty, musky, camphoraceous, rosy, green, spicy (cubeb/peppery), woody and caryophyllene-like aromas with buttery and spicy topnotes to soaps, liquid and solid cationic, anionic, nonionic or zwitterionic detergents, cosmetic powders, liquid and solid fabric softeners, perfumed polymers, polymers per se such as polyethylene and polypropylene, optical brightener compositions and other products. The amount employed can range up to 50% or higher and will depend on considerations of cost, nature of the end product, and the effect desired on the finished product and the particular fragrance sought.

The isopropyl substituted cyclohexenyl methyl ketones of our invention can be used alone or in a perfume composition as an olfactory component in detergents and soaps, space odorants and deodorants; perfumes; colognes, toilet waters; bath salts; hair preparations such as lacquers, brilliantines, pomades, and shampoos; cosmetic preparations such as creams, deodorants, hand lotions, and sun screens; powders such as talcs, dusting powders, face powder, and the like. When used as an olfactory component of a perfumed article, as little as 0.01% of one or more of the isopropyl substituted cyclohexenyl methyl ketones of our invention will suffice to impart, augment or enhance musty, musky, camphoraceous, rosy, green, spicy (cubeb/peppery), woody and caryophyllene-like aromas with buttery and spicy topnotes. Generally, no more than 0.8% is required in the ultimate perfumed article. Accordingly, the perfumed articles of our invention can contain from about 0.01% up to about 0.8% by weight of the perfumed article of the isopropyl substituted cyclohexenyl methyl ketones of our invention.

In addition, the perfume composition of our invention can contain a vehicle or carrier for the isopropyl substituted cyclohexenyl methyl ketones of our invention alone or with other ingredients. The vehicle can be a liquid such as an alcohol such as ethanol, a glycol such as propylene glycol, or the like. The carrier can be an absorbent solid such as gum (e.g., guar gum, xanthan gum or gum arabic) or components for encapsulating the composition such as gelatin (as by coacervation) or a urea formaldehyde prepolymer (to form a urea formaldehyde polymer wall around a liquid perfume center) which can be used to form a capsule wall surrounding the perfume oil.

The following examples serve to illustrate our invention and this invention is to be considered restricted thereto only as indicated in the appended claims.

All parts and percentages given herein are by weight unless otherwise specified.

EXAMPLE 1

PREPARATION OF 4-ACETYL-5-ISOPROPYL-1-METHYLCYCLOHEXENE AND 4-ACETYL-5-ISOPROPYL-2-METHYLCYCLOHEXENE

Reaction:

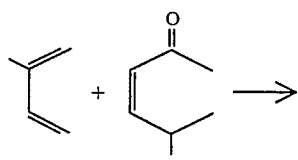

-continued
Reaction:

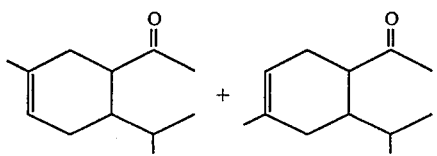

Into a 3 liter autoclave having a 1000 psig pressure rating is placed 748 grams of isoprene (11 moles) and 1234 grams (11 moles) of 2-methyl-3-hexen-5-one. The autoclave is sealed and heated to 150° C. at 300 psig pressure. The autoclave is operated at 250–300 psig pressure and 150°–180° C. for a period of 1.5 hours. At the end of the 1.5 hour period, the autoclave is cooled and opened.

The resulting reaction mass is then distilled on a fractionation column yielding the following fractions:

| Fraction No. | Vapor Temp. (°C.) | Liquid Temp. (°C.) | Vacuum mm/Hg. Pressure |
|---|---|---|---|
| 1 | 23/48 | 23/68 | 100/30 |
| 2 | 40 | 80 | 3.0 |
| 3 | 70 | 100 | 2.0 |
| 4 | 80 | 105 | 2.0 |
| 5 | 80 | 105 | 2.0 |
| 6 | 80 | 105 | 2.0 |
| 7 | 80 | 110 | 2.0 |
| 8 | 80 | 114 | 2.0 |
| 9 | 80 | 122 | 2.0 |
| 10 | 80 | 156 | 2.0 |
| 11 | 78 | 190 | 2.0 |

FIG. 1 is the GLC profile for the crude reaction product containing the "cis" and "trans" isomers of the compounds having the structures:

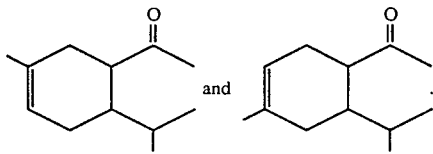

The peak indicated by reference number "10" is the peak for the "cis" and "trans" isomers of the compounds having the structures:

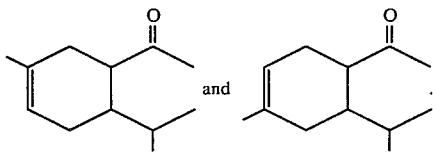

FIG. 2 is the NMR spectrum for the "cis" and "trans" isomers of the compounds having the structures:

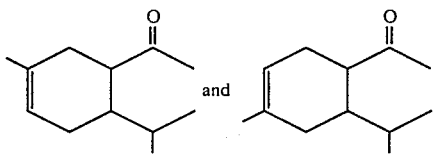

(conditions: Field strength: 100 MHz; Solvent: CFCl₃).

FIG. 3 is the infra-red spectrum for the "cis" and "trans" isomers of the compounds having the structures:

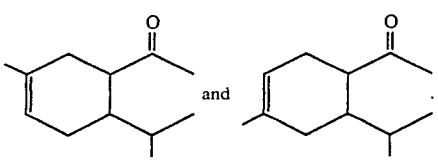

The resulting product, bulked fractions 3 to 11 of the foregoing distillation has an excellent musty, musky, camphoraceous, rosy and green aroma profile.

EXAMPLE II

PREPARATION OF
MIXTURE OF
4-ACETYL-5-ISOPROPYL-1,3-DIMETHYLCYCLOHEXENE AND
4-ACETYL-5-ISOPROPYL-2,6-DIMETHYLCYCLOHEXENE

Reaction:

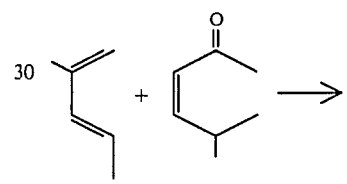

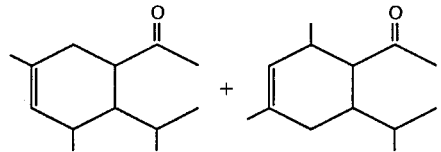

Into a 3 liter autoclave rated for 1000 psig pressure is placed 410 grams of 2-methyl-1,3-pentadiene (5 moles) and 570 grams of 2-methyl-3-hexen-5-one (5 moles). The autoclave is sealed and heated to 150° C. at a pressure of 200 psig and maintained at 150° C. and 200 psig pressure for a period of 2.0 hours.

The autoclave is then cooled and opened and the resulting product is distilled yielding the following fractions:

| Fraction No. | Vapor Temp. (°C.) | Liquid Temp. (°C.) | Vacuum mm/Hg. Pressure |
|---|---|---|---|
| 1 | 23/90 | 23/100 | 100/50 |
| 2 | 64 | 83 | 20.0 |
| 3 | 63 | 80 | 10.0 |
| 4 | 63 | 80 | 4.0 |
| 5 | 47 | 100 | 2.0 |
| 6 | 47 | 100 | 2.0 |
| 7 | 70 | 110 | 2.0 |
| 8 | 82 | 105 | 2.0 |
| 9 | 82 | 105 | 2.0 |
| 10 | 82 | 105 | 2.0 |
| 11 | 70 | 110 | 1.6 |
| 12 | 72 | 112 | 1.6 |
| 13 | 70 | 139 | 1.0 |
| 14 | 72 | 150 | 1.0 |

FIG. 4 is the GLC profile for the crude reaction product containing the compounds having the structures:

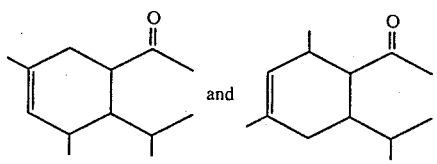
and (mixture of "cis" and "trans" isomers) (conditions: SE-30 column programmed at 160° C. isothermal). The peak indicated by reference numeral "40" is the peak for the "cis" and "trans" isomers of each of the compounds having the structures:

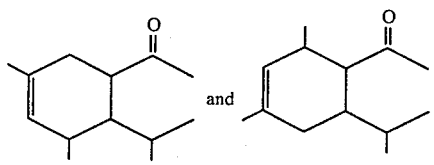
and

FIG. 5 is the NMR spectrum for the mixture of "cis" and "trans" isomers having the structures:

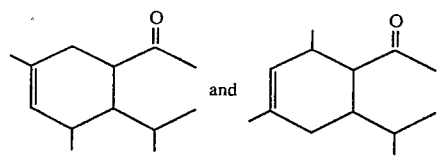
and (conditions: Field strength: 100 MHz; Solvent: CFCl$_3$).

FIG. 6 is the infra-red spectrum for the mixture of "cis" and "trans" isomers having the structures:

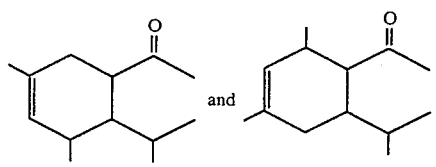
and

Bulked Fractions 5-13 has a spicy (cubeb/peppery), woody, camphoraceous and caryophyllene-like aroma profile.

EXAMPLE III

PREPARATION OF 4-ACETYL-5-ISOPROPYL-1-METHYLCYCLOHEXENE

Reaction:

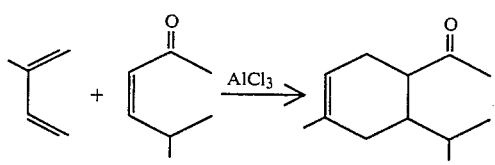

Into a 3 liter reaction vessel equipped with cooling coils, reflux condenser, thermometer, stirring apparatus and heating mantle is placed 800 grams of methylene chloride. The methylene chloride is cooled to 10° C. 160.2 Grams of anhydrous aluminum chloride is then added to the methylene chloride with stirring while maintaining the reaction mass at 10° C. Over at ten minute period, 784 grams of 2-methyl-3-hexen-5-one is added to the reaction mass with stirring while maintaining the reaction mass at 10° C. At the end of the addition of the 2-methyl-3-hexen-5-one over a period of two hours, 500 grams of isoprene is added to the reaction mass with stirring. During the two hour period, the temperature of the reaction mass rises from 10° C. up to 23° C. The reaction mass is then stirred at 23° C. for a period of two hours.

The reaction mass is then mixed with 1 liter of water and neutralized with 1 liter of 10% sodium bicarbonate.

The organic phase is then distilled on a 12" Goodloe fractionation column yielding the following fractions:

| Fraction No. | Vapor Temp. (°C.) | Liquid Temp. (°C.) | Vacuum mm/Hg. Pressure |
|---|---|---|---|
| 1 | 70 | 101 | 2.0 |
| 2 | 78 | 100 | 2.0 |
| 3 | 78 | 100 | 2.0 |
| 4 | 78 | 100 | 2.0 |
| 5 | 78 | 100 | 2.0 |
| 6 | 78 | 100 | 2.0 |
| 7 | 79 | 101 | 2.0 |
| 8 | 79 | 101 | 2.0 |
| 9 | 78 | 104 | 2.0 |
| 10 | 75 | 106 | 1.6 |
| 11 | 75 | 106 | 1.6 |
| 12 | 75 | 106 | 1.6 |
| 13 | 75 | 106 | 1.6 |
| 14 | 75 | 107 | 1.6 |
| 15 | 75 | 108 | 1.6 |
| 16 | 75 | 108 | 1.6 |
| 17 | 75 | 108 | 1.6 |
| 18 | 75 | 110 | 1.6 |
| 19 | 75 | 114 | 1.6 |
| 20 | 75 | 120 | 1.6 |
| 21 | 75 | 124 | 1.6 |
| 22 | 74 | 156 | 1.6 |

FIG. 7 is the GLC profile for the crude reaction product prior to distillation.

FIG. 8 is the GLC profile for bulked Fractions 10-19 of the foregoing distillation (conditions: SE-30 column programmed at 180° C. isothermal). The resulting reaction product contains the "cis" and "trans" isomers of the compound having the structure:

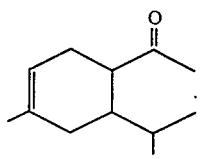

Bulked Fractions 10-19 has an excellent green, woody, rosy, musty, camphoraceous aroma with buttery and spicy topnotes.

FIG. 9 is the NMR spectrum for the "cis" and "trans" isomers of the compound having the structure:

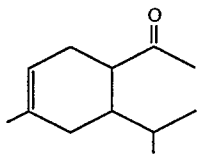

(conditions: Field strength: 100 MHz; Solvent: CFCl₃).

FIG. 10 is the infra-red spectrum for the mixture of "cis" and "trans" isomers having the structure:

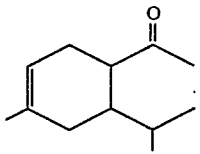

EXAMPLE IV

GREEN, FLORAL FRAGRANCE

The following mixtures are prepared:

| Ingredients | Parts by Weight | | |
|---|---|---|---|
| | IV(A) | IV(B) | IV(C) |
| 3-Phenyl-4-pentenal ethylene acetal | 3.0 | 3.0 | 3.0 |
| 3-Phenyl-4-pentenal diisobutyl acetal | 4.0 | 4.0 | 4.0 |
| 2-oxa-1,1,3,3-tetramethyl-2,3,5,6,7,8-hexahydro-1H—benz(f)-indene | 3.0 | 3.0 | 3.0 |
| Ylang extra | 5.0 | 5.0 | 5.0 |
| Geraniol coeur | 100.0 | 100.0 | 100.0 |
| Citronellol coeur | 70.0 | 70.0 | 70.0 |
| Dimethyl benzyl carbinol | 20.0 | 20.0 | 20.0 |
| Phenyl ethyl alcohol coeur | 30.0 | 30.0 | 30.0 |
| Hexyl cinnamic aldehyde | 30.0 | 30.0 | 30.0 |
| 2-n-Heptyl-cyclopentanone | 2.0 | 2.0 | 2.0 |
| Diels-Alder addition product of cyclopentadiene and 3-methyl-3-penten-2-one having the structure: | 20.0 | 20.0 | 20.0 |
| Linalyl acetate | 30.0 | 30.0 | 30.0 |
| n-Decanal | 2.0 | 2.0 | 2.0 |
| Geranonitrile | 30.0 | 30.0 | 30.0 |
| Orange terpeneless | 10.0 | 10.0 | 10.0 |
| Geranyl acetate | 20.0 | 20.0 | 20.0 |
| Lavender | 10.0 | 10.0 | 10.0 |
| Neroli oil | 10.0 | 10.0 | 10.0 |
| Mixture of compounds having the structures: ("cis" and "trans" isomers) produced according to Example I. | 12.0 | 0.0 | 0.0 |
| Mixture of isomers having the structures: ("cis" and "trans" isomers) produced according to Example II. | 0.0 | 12.0 | 0.0 |
| Mixture of "cis" and "trans" isomers having the structure: produced according to Example III. | 0.0 | 0.0 | 30.0 |

The mixture of compounds having the structures:

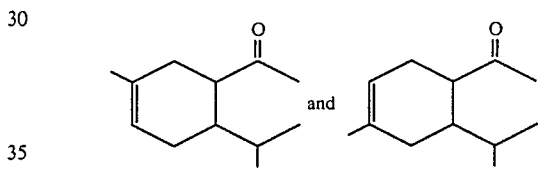

(mixture of "cis" and "trans" isomers) prepared according to Example I adds an interesting musty, musky, camphoraceous and rosy aroma profile to this green, floral fragrance. Accordingly, the fragrance can be described as "green, floral with musty, musky, camphoraceous and rosy undertones".

The mixtures of compounds having the structures:

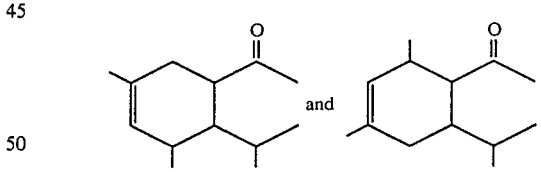

(mixture of "cis" and "trans" isomers) imparts to this green, floral fragrance a spicy, woody, camphoraceous and caryophyllene-like undertone. Accordingly, the resulting fragrance can be described as "green and floral with spicy, woody, camphoraceous and caryophyllene-like undertones".

The mixture of "cis" and "trans" isomers having the structure:

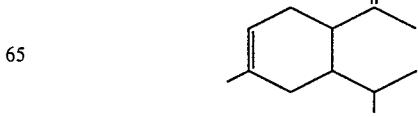

produced according to Example III imparts to this green, floral fragrance, a woody, rosy, musty and camphoraceous undertone with buttery and spicy topnotes. Accordingly, the resulting fragrance can be described as "green, floral with woody, rosy, musty and camphoraceous undertones and buttery and spicy topnotes".

EXAMPLE V

PREPARATION OF A COSMETIC POWDER COMPOSITION

A cosmetic powder is prepared by mixing in a ball mill 100 grams of talcum powder with 0.25 grams of each of the perfume substances set forth in Table II below. The resulting cosmetic powders have excellent aroma profiles as indicated in Table II below.

TABLE II

| Perfume Substance | Aroma Profile Imparted |
|---|---|
| Mixture of "cis" and "trans" isomers of the compounds having the structures: 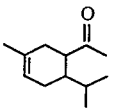 and 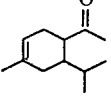 prepared according to Example I. | A musty, musky, camphoraceous, rosy and green aroma profile. |
| A mixture of compounds having the structures: 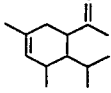 and 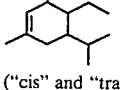 ("cis" and "trans" isomers) produced according to Example II. | A spicy (cubeb/peppery), woody, camphoraceous and caryophyllene-like aroma profile. |
| The compound having the structure: 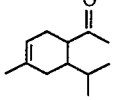 (mixture of "cis" and "trans" isomers) produced according to Example III. | A green, woody, rosy, musty and camphoraceous aroma with buttery and spicy topnotes. |
| Perfume composition of Example IV(A). | A green, floral with musty, musky, camphoraceous and rosy undertones. |
| Perfume composition of Example IV(B). | A green and floral with spicy, woody, camphoraceous and caryophyllene-like undertones. |
| Perfume composition of Example IV(C). | A green, floral with woody, rosy, musty and camphoraceous undertones and buttery and spicy topnotes. |

EXAMPLE VI

PREPARATION OF SOAP COMPOSITION

100 Grams of soap chips are mixed with 1 gram of each of the perfume materials of Table II of Example V until a substantially homogeneous composition is obtained. The resulting mixture is melted and maintained at 10 atmospheres pressure at a temperature of 180° C. for a period of 4 hours. At the end of the 4 hour period, the resulting homogeneous mixture is cooled. The perfumed soap composition manifests an excellent aroma character as set forth in Table II of Example V.

EXAMPLE VII

PREPARATION OF A DETERGENT COMPOSITION

A granular detergent composition is prepared according to Example 9 of Canadian Pat. No. 1,004,566 (the diclosure of which is incorporated by reference herein) containing the following ingredients:

| Component | Weight % |
|---|---|
| Anhydrous sodium carbonate | 30.0 |
| Hydrated sodium silicate (81.5% solids, $SiO_2:Na_2O$ ratio-2.1:1 by weight) | 20.0 |
| Coconut alcohol condensed with 6 molar proportions of ethylene oxide | 10.0 |
| Sodium citrate dihydrate | 10.0 |
| Sodium dichlorocyanurate dihydrate | 3.8 |
| Polyethylene glycol (available under the trademark Carbowax 4000, M.W. 3000-3700) | 2.0 |
| Dimethyl silicone | 0.8 |
| Anhydrous sodium sulfate | 15.5 |
| Perfume substance as set forth in Table II of Example V. | 5.9 |

The resulting detergent compositions have excellent aromas as set forth in Table II of Example V.

EXAMPLE VIII

PREPARATION OF DETERGENT COMPOSITION

A detergent is prepared from the following ingredients according to Example I of Canadian Pat. No. 1,007,948 (the disclosure of which is incorporated herein by reference):

| Ingredients | Parts by Weight |
|---|---|
| Neodol 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. A total of 100 grams of this detergent is admixed individually with 0.15 grams of each of the perfumery substances of Table II of Example V, supra. Each of the detergents has excellent aromas as set forth in Table II of Example V.

EXAMPLE IX

PERFUMED LIQUID DETERGENT

Concentrated liquid detergents with aroma nuances as set forth in Table II of Example V containing a 0.10%, 0.15% and 0.20% of each of the perfumery substances of Table II of Example V are prepared. They are prepared by adding and homogeneously admixing the appropriate quantity of each of the perfumery substances of Table II of Example V in the liquid detergent. The detergents all possess excellent aromas as set forth in Table II of Example V.

EXAMPLE X

COLOGNE AND HANDKERCHIEF PERFUMES

The perfume substances of Table II of Example V are each incorporated separately into colognes at concentrations of 1.5%, 2.0%, 2.5%, 3.0%, 4.0% and 5.0% in 70%, 75%, 80%, 85% and 90% aqueous ethanol solutions; and into handkerchief perfumes at concentrations of 15%, 20%, 30% and 40% (in 80%, 85%, 90% and 95% aqueous ethanol solutions). Distinct and definitive strong fragrances are imparted to the colognes and to the handkerchief perfumes at the levels indicated according to the aroma profiles as set forth in Table II of Example V.

EXAMPLE XI

Utilizing the procedure of Example I of column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57 percent C$_{20-22}$ HAPS
   22 percent isopropyl alcohol
   20 percent antistatic agent
   1 percent of the oxabicyclooctane derivative or cyclohexyl alkyl or alkenyl carbinol or ester thereof of our invention as set forth in the Table II of Example V and giving rise to the aroma nuances as set forth in said Table II of Example V.

Fabric-softening compositions prepared as set forth above having the above aroma characteristics essentially consist of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The aromas as set forth in Table II of Example V, supra above are imparted in a pleasant manner to the head space in the dryer on operation thereof using the said dryer added fabric softening nonwoven fabric.

What is claimed is:

1. An isopropyl substituted cyclohexenyl methyl ketone defined according to the structure:

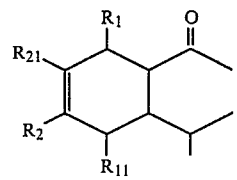

wherein $R_1$, $R_2$, $R_{11}$ and $R_{21}$ each represents hydrogen or methyl with the provisos that:
   (a) at least two of $R_1$, $R_{21}$, $R_2$ and $R_{11}$ represent hydrogen;
   (b) either $R_2$ is methyl and $R_{21}$ is hydrogen or $R_{21}$ is methyl and $R_2$ is hydrogen; and
   (c) $R_1$ is methyl only when $R_2$ is methyl and $R_{11}$ is methyl only when $R_{21}$ is methyl.

2. A mixture of isopropyl substituted cyclohexenyl methyl ketones defined according to claim 1 having the structures:

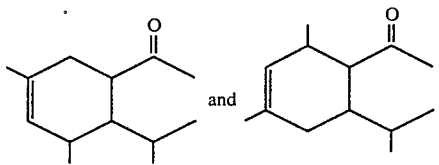

3. A mixture of isopropyl substituted cyclohexenyl methyl ketones defined according to claim 1 having the structures:

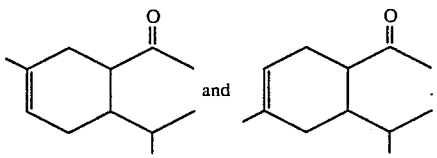

4. An isopropyl substituted cyclohexenyl methyl ketone defined according to claim 1 having the structure:

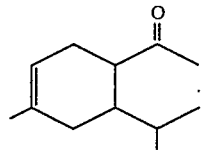

5. A process for augmenting or enhancing the aroma of a consumable material selected from the group consisting of perfume compositions, colognes and perfumed articles comprising the step of intimately admixing with said consumable material an aroma augmenting or enhancing quantity of at least one isopropyl substituted cyclohexenyl methyl ketone defined according to claim 1.

6. The process of claim 5 wherein the consumable material is a perfume composition, cologne or perfumed polymer.

7. The process of claim 5 wherein the consumable material is a perfumed article and the perfumed article is a solid or liquid anionic, cationic, nonionic or zwitterionic detergent.

8. The process of claim 5 wherein the consumable material is a perfumed article and the perfumed article is a fabric softener composition or fabric softener article.

9. The process of claim 5 wherein the isopropyl substituted cyclohexenyl methyl ketones is a mixture of compounds having the structures:

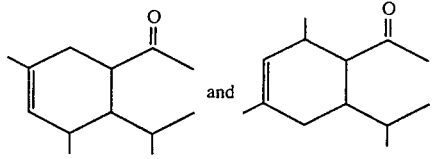

10. The process of claim 5 wherein the isopropyl substituted cyclohexenyl methyl ketones is a mixture of compounds having the structures:

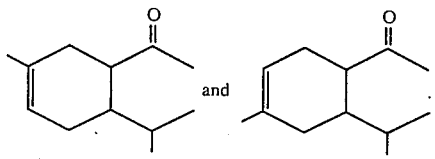

11. The process of claim 5 wherein the isopropyl substituted cyclohexenyl methyl ketones has the structure:

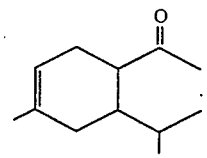

* * * * *